United States Patent
Samuelsson et al.

(10) Patent No.: US 7,050,857 B2
(45) Date of Patent: May 23, 2006

(54) PROGRAMMING SYSTEM FOR MEDICAL DEVICES

(75) Inventors: Eric Samuelsson, Järfälla (SE); Jonas Andersson, Johanneshov (SE)

(73) Assignee: St. Jude Medical AB (SE)

( * ) Notice: Subject to any disclaimer, the term of this patent is extended or adjusted under 35 U.S.C. 154(b) by 584 days.

(21) Appl. No.: 10/149,664

(22) PCT Filed: Dec. 12, 2000

(86) PCT No.: PCT/SE00/02520

§ 371 (c)(1),
(2), (4) Date: Nov. 6, 2002

(87) PCT Pub. No.: WO01/43822

PCT Pub. Date: Jun. 21, 2001

(65) Prior Publication Data

US 2003/0176899 A1 Sep. 18, 2003

(30) Foreign Application Priority Data

Dec. 16, 1999 (SE) .................................. 9904627

(51) Int. Cl.
*A61N 1/08* (2006.01)

(52) U.S. Cl. ........................................ 607/60; 607/59

(58) Field of Classification Search .................. 607/30, 607/32, 59, 60
See application file for complete search history.

(56) References Cited

U.S. PATENT DOCUMENTS

| 5,713,937 A | * | 2/1998 | Nappholz et al. ............. 607/30 |
| 5,800,473 A | | 9/1998 | Faisander |
| 5,833,623 A | | 11/1998 | Mann et al. |

* cited by examiner

*Primary Examiner*—Angela D. Sykes
*Assistant Examiner*—Roderick Bradford
(74) *Attorney, Agent, or Firm*—Schiff Hardin LLP

(57) ABSTRACT

In a programmer for an implantable medical device, a method for operating and controlling a implantable medical device, and in a computer software product, a graphical representation of a quantity influenced by the operation of the medical device is displayed, and parameters relating to the control of the device are associated with portions of the graphical representation. When an operator selects and alters the shape of the displayed graphical representation to illustrate a desired operational effect of the medical device on the quantity, a value associated with the altered shape is automatically modified and communicated to the implanted medical device. The operator thus is able to select parameters on the basis of the intended effect, rather than setting parameter values and then observing the effect.

23 Claims, 3 Drawing Sheets

PROGRAMMING SYSTEM FOR MEDICAL DEVICES

BACKGROUND OF THE INVENTION

1. Field of Invention

The invention relates generally to implantable medical devices and more particularly to systems for programming implantable medical devices.

2. Description of the Prior Art

Implantable medical devices perform multiple highly complex functions which may be adapted to the particular conditions and needs of specific patients. For example implantable cardiac pacers, which provide stimulating impulses to a heart with a disturbed cardiac rhythm, can be configured with various different parameters values and functions depending on the particular condition of a patient. As an example, a cardiac pacer that is presently on the market allows in excess of 40 different parameters to be programmed.

In addition to the programmable parameters, a cardiac pacer generally stores a large quantity of measured data. Conventional pacers are commonly equipped with sensors for monitoring the activity of the heart. Information obtained though monitoring can be used for diagnosing certain patient conditions, which in turn can be addressed by adapting the pacer functions in some way. The programming and interrogation of implanted devices is commonly performed non-invasively using a computer- or microprocessor-based programmer, which communicates with the pacer via a telemetry link. These programmers include a display and some form of keyboard, which may be implemented as a touch sensitive screen, for the input of data. When the programmer interrogates the implanted device, stored and measured data will be transferred to the programmer.

This information must be displayed to the operator. Parameter values, whether programmable, measured or fixed, are displayed as numerical or alphanumerical values. An example of such a programmer is described in U.S. Pat. No. 5,833,623. The manner in which this information is organized for display varies from programmer to programmer. U.S. Pat. No. 5,713,937 describes a programmer where characteristics in a graph illustrating an ECG can be added to the graph by selecting and dragging icons from a menu bar to the graph. However, conventional programmers typically display programmable parameters and measured data separately. Moreover, with the large amount of data provided by present day pacers, the programmable information in many cases is further divided into subgroups for display. For example, programmable parameters may include basic parameters, extended parameters, sensor parameters and patient data. Such groupings are typically chosen for technical reasons related to the internal organization of the programmer. For example some parameters may require additional interrogation of the pacer, while others may be more readily available. Consequently, an operator of a programmer must be very familiar with the programmer organization if he is to operate the programmer effectively and to full effect.

The majority of such medical devices are programmed and monitored by medically skilled practitioners, who have a thorough understanding of the patient's condition, but may have less knowledge of the possibilities of the programmer and/or the medical device. Moreover, they may be required to monitor several different types of medical devices, working in different modes and implanted in patients with different diagnoses. As a result, an operator may encounter two medical devices of the same type and configured in the same way for the same patient diagnosis only infrequently. Consequently, there is a need for a programmer that is simple to operate and which can be used intuitively.

SUMMARY OF THE INVENTION

It is thus an object of the invention to provide a programmer for monitoring and controlling the operation of an implantable device that is easy to operate, and thus enables an operator to exploit all possible functions of a medical device with little knowledge of the programmer.

It is a further object of the invention to provide a programmer that provides the operator with an interface to the medical device that is easy to understand and operate, and thus enables a operator to exploit all possible functions of a medical device with little knowledge of the programmer.

These objects are achieved in accordance with the invention in an arrangement for monitoring and controlling the operation of an implantable medical device, having a communication unit for communicating with said medical device, a display for displaying a graphical representation of a quantity influenced by the operation of the medical device, an association unit for associating parameters relating to the control of the device with portions of the graphical representation, a selection unit for selecting and moving points in the graphical representation to thereby alter the shape of the displayed graphical representation to illustrate a desired operational effect of the medical device on the quantity, and a modifier unit responsive to the altered shape for modifying the values of associated parameters in accordance with the modification of the portions.

By linking parameters to a graphical representation of a quantity influenced by the operation of the medical device, the operator will be able to select parameters on the basis of the effect intended, rather than setting parameters and then observing the effect. The resulting system thus not only is more intuitive and thus easier to use for a medical practitioner, also is safer for the patient, since there is less likelihood of the operator programming unsuitable parameter values.

Preferably the quantity is a measurable physiological activity commonly used for evaluating the condition of the patient. For example, when the medical device is a cardiac stimulating device, a useful quantity for use in programming the device control parameters is the electrical activity of the heart in the form of an electrocardiogram (ECG) or intracardial electrogram (IEGM), which is commonly measured by the device or the programmer and serves as an important diagnostic tool for evaluating the condition of the patient and the operation of the implanted device. Other waveforms, for example showing the variation of the quantity over time, are also useful for programming parameter values.

Obviously, some implanted devices will only permit specific discrete parameter values to be used. The programming arrangement thus advantageously includes means for setting a nearest authorized modified parameter value in response to the altered shape of the graphical representation.

The graphical representation may be a stored representation of the quantity. Advantageously, however, the arrangement includes a data collecting arrangement for collecting data relating to the quantity, and a unit for constructing a graphical representation of the quantity for display. In this way any desired effect expressed by that manipulation of the graphical representation will be more closely related to the actual effect achieved after modification of the parameters.

Preferably, several parameters are associated with portions of the same graphical representation, such that any alteration in shape of the graphical representation causes the modification of all parameters at the same time. This not only saves time, but also enables the illustration of any naturally existing interdependence between parameters, which results in a more intuitive and understandable procedure for a clinician.

The invention further relates to a method for monitoring and controlling the operation of an implantable medical device and also to a computer program product.

DESCRIPTION OF THE PREFERRED EMBODIMENTS

Figure 1:
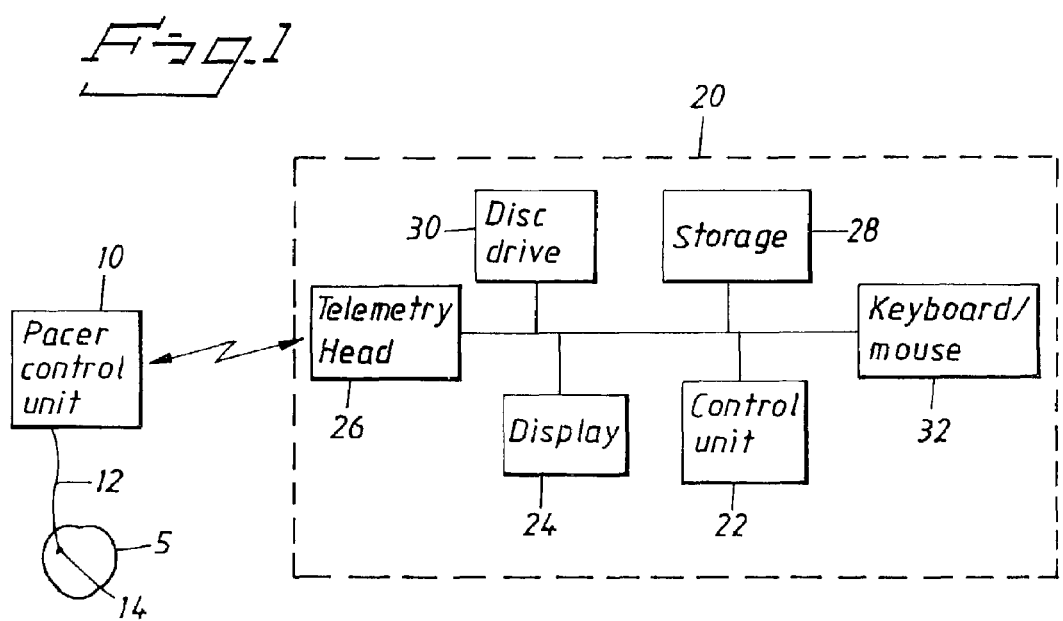
FIG. 1 schematically shows a system for programming a medical device in accordance with the present invention.

FIG. 1 schematically shows an arrangement for programming an implanted medical device. In the illustrated embodiment, the medical device is a cardiac pacer implanted in a patient. The pacer has a pacer control unit 10, which is generally implanted pectorally near the shoulder of the patient under the skin and one or more electrodes 14, which are anchored in the patient's heart 5. One or more leads 12 connect the electrodes 14 to the pacer control unit 10. The pacer is capable of operating autonomously and is powered by a battery (not shown). The electrodes 14 are used to apply stimulating pulses to the heart tissue and may also sense the electrical activity of the heart and possibly other physiological activities, such as respiration. This information is stored in the pacer control unit 10, for example in the form of an intracardial electrogram (IEGM) for later consultation by a medical practitioner during a routine check. Other information collected and stored in the pacer control unit 10 can include data relating to the condition of the pacer, such as the residual battery power or the impedance of the leads 12. The information stored in a pacer can be consulted using a programmer 20 which is preferably computer- or microprocessor based.

The programmer 20 includes a control unit 22, a display 24, a telemetry head 26, internal storage unit 28 and some form of data input device 32 that may be a keyboard, a mouse, a touch-sensitive screen, or the like, or some combination of these. A disk drive 30 may also be provided in the programmer 20 for receiving a diskette, CD ROM or similar portable storage element capable of carrying computer-readable code. Software used for controlling the operation of the programmer is stored in the storage unit 28 ad executed by the control unit 22 using the storage unit 28. Additional software applications can be provided on a removable diskette and read with the aid of the disk drive 32. These additional software applications may be used to optionally extend the functions of the programmer. Alternatively, additional software applications may assure more basic functions that are specific to a class of implantable device; this may be of interest when the internal storage unit 28 of the programmer 20 are of limited capacity, for example. Communication between the programmer 20 and the pacer control unit 10 is effected via a telemetry link, whereby the telemetry head 26, which preferably includes an inductive coil, is placed over the implantation site of the pacer control unit 10. Once a link has been established, the programmer 20 interrogates the pacer control unit 10 and downloads the stored information. Modifications to the pacer settings programmed by the programmer 20 are also uploaded to the pacer control unit via the telemetry link. Exchanges of information between the pacer control unit 10 and the programmer 20 may occur throughout a programming session, for example to obtain recent ECG or IEGM signals recorded by the pacer 10 when testing a modified parameter value.

Interaction between the operator and the programmer 20 is through the display 24 and input device 32 and more particularly through a graphical user interface of the programmer 20. Through the graphical user interface, the operator may use the programmer 20 to set programmable parameter values, carry out tests on the implantable device and also view diagnostic data.

In accordance with the present invention, the programmer 20 displays parameter values in graphical form. More specifically, the programmer 20 displays a representation of a quantity that is influenced by the operation of the implanted medical device. Preferably this quantity is also measured by the implanted medical device. Preferably the quantity represents a physiological activity influenced by the device and commonly used by a clinician for evaluating the patient's condition and also the operation of the implanted device 10. The parameters used for controlling the operation of the medical device are mapped to this representation in such a way that a variation in the shape of the representation causes the programmer to effect a corresponding variation in the value of the mapped parameters. The representation of a physiological activity is preferably in the form of a waveform. In the present example which relates to a cardiac pacer 10, the waveform is an ECG or IEGM, which is routinely measured during programmer sessions. Data representing the measured electrical activity of the heart in the form of an ECG or IEGM is also readily available from the pacer device itself. By displaying parameters in such a graphical form, and moreover, permitting the modification of parameters by manipulating the graphical representation, the operator knows immediately what effect the programmed parameters will have on the patient's condition. This is described in more detail with reference to FIG. 2.

Figure 2:
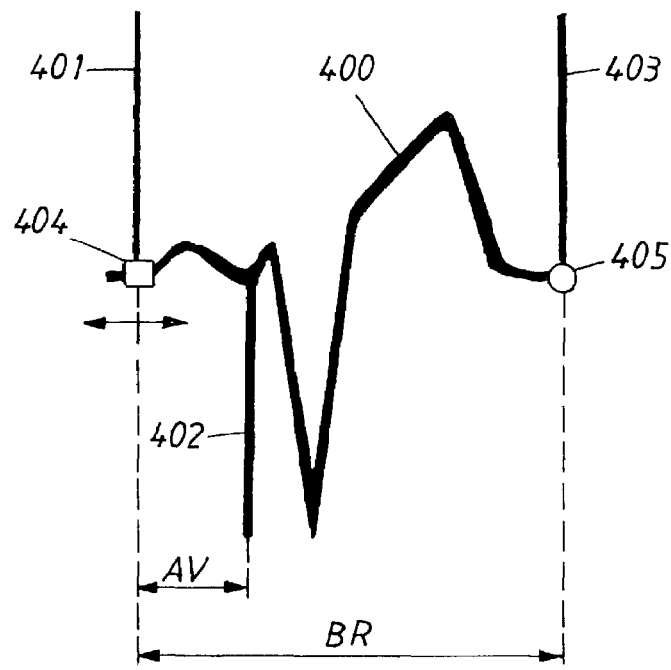
FIG. 2 shows a window of the graphical user interface for programming AB delay and base rate in accordance with the invention.

FIG. 2 shows a parameter programming window of the graphical user interface. It is assumed that this window is displayed by the programmer following the selection by the operator of the programmable parameter in a graphical user interface of the programmer 20. The parameter selected is the base rate of the pacer 10.

The waveform 400 depicted in this window represents one cycle of an ECG in which atrial stimulation pulses 401 and ventricular stimulation pulses 402 are shown. The atrial stimulation pulse 403 for the following cycle is also shown in the waveform. For this waveform, the programmable parameter for the basic interval BR of the pacer is mapped to the distance between the two atrial stimulation pulses 401, 403. The basic interval is the period between two consecutive paced events without intervening intrinsic activity. While the basic interval is not a common programmable parameter for most pacers, it is inversely proportional to the base rate, which is commonly used. The programmer may associate either base rate values or basic interval values with this distance. A further parameter, namely the AV delay, AV, is also mapped to a portion of the waveform, specifically to the distance between the first atrial stimulation pulse 401 and the ventricular stimulation pulse 402. Select points on the curve are defined as movable or fixed. In FIG. 2, the starting point 404 represented by a square is a movable point, while the end point 405 represented by a circle is a fixed point. By selecting and dragging the movable point 404, either using a cursor control device, such as a mouse, or by keyboard or keypad controls, the operator can alter the length of the curve 400, and specifically the mapped portions of the curve. Since both the basic interval BR and the AV delay AV depend on distances measured in parallel to the horizontal axis of the curve 400, the movable point 404 is constrained to move along a straight line defined by the axis (the time axis) of the curve 400.

The programmer 20, and specifically the control unit 22 automatically adjusts the parameter values linked to the dimensions of the curve 400. For example if the operator moves the movable point to the left in FIG. 2 to lengthen the curve, the basic interval will be lengthened and the base rate reduced accordingly. Similarly, a reduction in the curve length by moving the movable point to the right in the figure will reduce the basic interval. Once an operator has made the desired adjustment to the curve, he may program the pacer device 10 with the associated parameter values. This is preferably achieved by providing a separate "program" command button on the screen. On registering this command, the control unit 22 of the programmer 20 sends the new parameter values to the pacer device 10 through the telemetry head 26. Only basic interval or base rate values allowed by the pacer device will be programmed. Thus if the pacer permits specific discrete values of base rate only, the programmer will set the permitted value that is closest to that defined by the modified curve. In the same way, the upper and lower limits of any parameter value is similarly observed. The upper and lower limits of a parameter are preferably also illustrated graphically by preventing further movement of the curve when a limit has been reached. In addition, the two end points of any parameter value may be illustrated graphically as limits to the curve variation to aid the operator in scaling any adjustment.

When the movable point 404 of the curve is shifted, this causes a stretching of the curve throughout its length. Thus all the intervals defined along its length will be modified in scale with the increase in length. In other words, the curve 400 retains its relative proportions in the direction of movement in analogy with normal physiological processes. Thus in the curve depicted in FIG. 2, an increase in the basic interval BR or reduction of the base rate caused by the extension of the curve width will automatically cause an in-scale variation of the AV delay (interval). When the operator programs a modified base rate, the control unit 22 will automatically send the adjusted AV delay value to the pacer 10. Other parameters that are likewise affected by a variation in the basic interval, such as the PV delay or the refractory period, could also be associated with the curve. This permits different parameters to be altered and programmed using the same curve. For example supposing that at a base rate of 90 pulses per minute (ppm), the AV interval must not exceed 300 ms. The restriction in the value of AV delay may be automatically implemented by the programmer when the operator adjusts the base rate by altering the total length of the curve 400.

Different parameters may also be programmed independently using the same curve. For the programming of each separate parameter, a different set of fixed 405 and movable points 404 are displayed. The different programmable parameters may be selected by the operator using an appropriate command from a menu bar incorporated in the parameter programming window. Alternatively, or in addition, the desired parameter may be selected by selecting the appropriate portion of the curve 400 to make movable 404 ad fixed points 405 appear.

Figure 3:
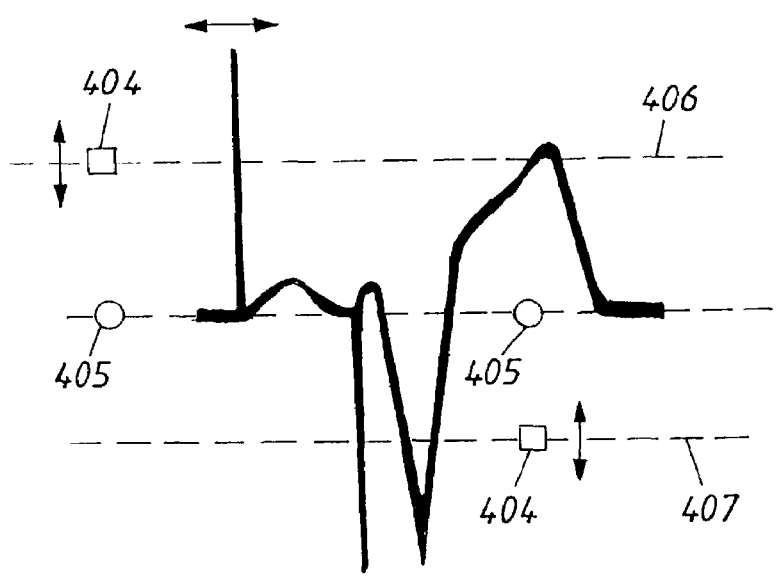
FIG. 3 shows a window of the graphical user interface for programming capture threshold and evoked response sensitivity in accordance with the present invention.

The representation of parameters in terms of their effect on a physiological activity as illustrated in FIG. 2 is preferably also utilized for the depiction of diagnostic tests and measured data. This is shown as an example in FIG. 3 which shows a further screen of the graphical user interface. Here the same curve 400 is depicted as in FIG. 2. Two threshold levels 406, 407 are shown in the form of horizontal lines. The uppermost line 406 in FIG. 3 represents the atrial capture threshold and the lower line 407 represents the evoked response (ER) sensitivity threshold, which relates to ventricular stimulation. Fixed points 405 are located on the central horizontal axis of the curve 400. Movable points 404 are located on the lines 406, 407. These lines 406, 407 are thus movable with respect to the central (horizontal) axis of the curve, whereby an increase in the distance between a threshold line and the central axis causes an increase in threshold value, and a decrease in distance results in a decrease in threshold value. In the illustrated example, the evoked response sensitivity threshold value 407 can be viewed or set by moving the line. The atrial capture threshold is preferably used to indirectly adjust the atrial pulse width, and so adjust the atrial pulse energy. Reducing the threshold level by moving the line 406 towards the central axis of the curve 400 results in an increase in the atrial pulse width, while an increase in the threshold level 406 causes a reduction in atrial pulse width.

For the example of a cardiac pacer described with reference to FIGS. 2 and 3, it is possible to represent substantially all programmable parameters and illustrate all tests utilizing waveforms which are graphical representations of a ECG cycle showing pacer stimulation pulsed and a ECG waveform of spontaneous activity.

Figure 4:
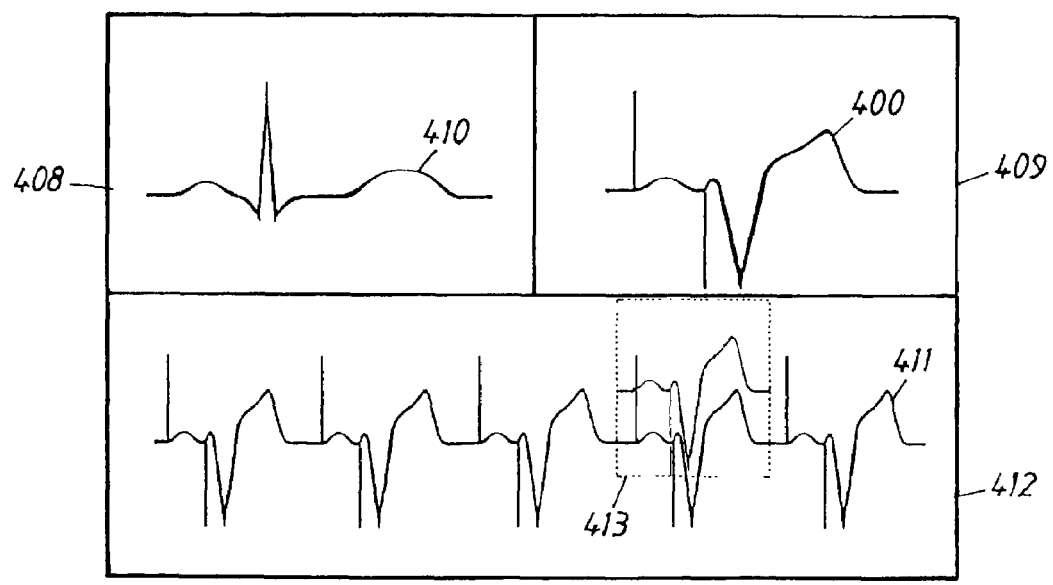
FIG. 4 shows a screening of the graphical user interface for programming parameter values according to a further embodiment of the invention.

As mentioned above, the waveform used to represent programmable parameters of an implanted medical device 10 may be derived from data collected by the device 10 itself or even from the programmer 20. Thus, for example, a programmer 20 of an implantable cardiac pacer 10 may utilize ECG or IEGM curves which are routinely recorded by the pacer 10 and sometimes by programmer 20 during follow-up visits by the patient at a clinic or surgery to depict the parameters. This brings with it the possibility of utilizing a waveform that is generated from the recorded data, to provide a real picture of the effects of programming parameters. This possibility is utilized in a further embodiment of the invention using a parameter programming screen as depicted in FIG. 4. The screen in FIG. 4 is divided into an upper and a lower portion, with two windows 408, 409 in the upper portion and a single window 412 in the lower portion. The two upper windows 408, 409 show waveforms used for programming parameters. The waveform 400 representing an ECG cycle showing atrial and ventricular stimulation is depicted in the right-hand upper window 409 and a waveform 410 representing a spontaneous ECG cycle 410 is depicted in the left-hand upper window 408. As mentioned above, these two waveforms 400, 410 can be used to program substantially all programmable parameters of a cardiac pacer, as well as illustrating tests and diagnostics. In the third window 412 depicted in the lower half of the screen there is displayed a continuously rolling waveform 411 constructed from data recorded by the pacer device or the programmer. The operator changes the shape of the waveforms 400, 410 in the two uppermost windows 408, 409 to program parameters and can observe the result on the recorded waveform 411 depicted in the lower window 412. In order to compare the results between the desired programmed values input via the waveforms 400 or 410 and the resulting measured waveform 411, the programming waveforms 400 and 410 may be copied and superimposed on parts of the measured waveform 411. This is illustrated in the lower window 412 of FIG. 4. Preferably this is implemented using a drag and drop function so that the operator may simply select the programming waveform 400, 410 and drag this down to the measured waveform 412 for comparison. The displaced waveform is automatically modified to the scale of the measured waveform 412 to enable a useful comparison. A freeze function is associated with the recorded waveform 411 and may be invoked to facilitate this comparison.

The waveforms 400 and 410 may be stylized waveforms stored in the programmer before use. Alternatively, the waveforms 400 and 410 may be generated from data recorded by the pacer device 10 or the programmer 20 some time previously or during programming of the cardiac pacer 10. This may be achieved in different ways. For example, when the programmer 20 is started, the initial waveforms 400, 410 displayed in the uppermost windows 408 and 409 will be simulated waveforms that are stored in the programmer 20. As a follow-up procedure progresses and measured data is obtained from the cardiac device 10 or the programmer 20, the waveforms 400 and 410 are replaced by a waveform based on the measured data. For example, the stimulated ventricular pulse amplitude may be measured by the pacer output stage. This values combined with the IEGM measured by the pacer 10 can then be combined to form a waveform 400 for programming. Since the measured ECG or IEGM waveform will vary slightly from cycle to cycle, the displayed waveforms 400 and 410 may be generated using the averaged data for several measured ECG or IEGM cycles.

Figure 5:
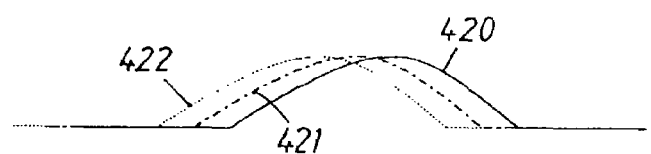
FIG. 5 illustrates a variation of the embodiment of FIG. 3.

In a further embodiment of the invention, the effects of varying the parameters as described with reference to FIGS. 3 and 4 is not shown using a continuously varying waveform as depicted in the lower window of FIG. 4. Rather the most recently available single waveform cycle is depicted with a number of earlier cycles shown offset from the most recent cycle. This is illustrated in FIG. 5. A current waveform 420 is depicted by a continuous line, earlier cycles 421 and 422 are depicted with dashed lines. In addition to being offset, earlier cycles are preferably also depicted in a contrasting shade or color as illustrated by the different broken lines in FIG. 5. This provides the operator with immediate feedback of the effects of altering one or more parameters.

In the exemplary embodiment using a programmer for a cardiac pacer, the parameters are linked to a representation of an ECG or IEGM signal. It will be appreciated that a measured or simulated ECG or IEGM waveform could equally be used to control intracardial devices (ICD) and devices for emerging indications (EI), for instance. In the case of devices for emerging indications (EI), which stimulate both sides of the heart, IEGM curves representing or measured from different sides of the heart can be compared and manipulated relative to one another to modify parameters that control the timing between the sides of the heart. It will be understood that the invention is not limited to ECG or IEGM waveforms. Any quantity that may be represented graphically and that is influenced by or influences the operation of an implantable medical device can be used for programming the device. The choice of quantity depends on the workings of the device and the types of parameters to be programmed. For example programmers for drug pumps may utilize a representation of the heart rate or respiration rate, neurostimulators may utilize waveforms representing electrical activity in the brain.

Although modifications and changes may be suggested by those skilled in the art, it is the invention of the inventors to embody within the patent warranted heron all changes and modifications as reasonably and properly come within the scope of their contribution to the art.

The invention claimed is:

1. An arrangement for monitoring and controlling operation of an implantable medical device, comprising:
    a communication unit adapted for communicating with a medical device located remote from said communication unit;
    a display at said communication unit for displaying a graphical representation of a quantity influenced by operation of said medical device;
    an association unit at said communication unit for associating parameters relating to control of said medical device with respective shapes of portions of said graphical representation and with relationships between respective portions of said graphical representation;
    a manually operable selector unit at said communication unit allowing an operator to directly select and move at least one point for selecting and moving points in said graphical representation to alter at least one of said shapes or said relationships to illustrate a desired operational effect of said medical device on said quantity; and
    a modification unit responsive to said altered shape or relationship for modifying values of the associated parameters dependent on the alteration of the shape or relationship of said displayed graphical representation to obtain modified values, said modified values being communicated to said medical device by said communication unit.

2. An arrangement as claimed in claim 1 wherein said display is a display for displaying a graphical representation of at least one physiological activity influenced by said medical device.

3. An arrangement as claimed in claim 1 wherein said modification unit modifies said values of said associated parameters by setting a nearest authorized modified parameter value dependent on said altered shape of said graphical representation.

4. An arrangement as claimed in claim 1 wherein said display comprises a display for displaying said graphical representation including a waveform.

5. An arrangement as claimed in claim 4 wherein said display displays said waveform as a variation of said quantity relative to time.

6. An arrangement as claimed in claim 1 further comprising a data collection system in communication with said communication unit, for collecting data relating to said quantity, and wherein said display includes circuitry for constructing said graphical representation of said quantity dependent on the collected data.

7. An arrangement as claimed in claim 1 wherein a plurality of parameters are associated with portions of a single graphical representation, and wherein said modification unit modifies respective values of all of said plurality of parameters dependent on said altered shape of said graphical representation.

8. An arrangement as claimed in claim 1 wherein said display unit displays a graphical representation of a waveform representing electrical activity of a cardiovascular system of a subject in which said medical device is implanted.

9. An arrangement as claimed in claim 1 wherein said communication unit is adapted to communicate with an implanted cardiac stimulating device, as said medical device.

10. A method for monitoring and controlling operation of an implantable medical device, comprising the steps of:
   displaying a graphical representation of a quantity influenced by operation of a medical device;
   mapping parameters relating to control of said medical device onto selected shapes and relationships of portions of said graphical representation;
   manually altering a shape or relationship of at least one of said portions of said graphical representation, by directly selecting and moving at least one point in said graphical representation, to display a desired operational effect of said medical device on said quantity;
   modifying a control parameter mapped to said graphical representation dependent on said altered shape or relationship, to obtain a modified parameter; and
   communicating said modified parameter to said medical device.

11. A method as claimed in claim 10 comprising displaying a quantity representing at least one physiological activity of a subject in whom said medical device is implanted.

12. A method as claimed in claim 10 wherein the step of mapping parameters comprises mapping magnitudes of parameters with selected dimensions of said graphical representation, and wherein the step of modifying a control parameter comprises modifying the magnitude of a control parameter dependent on a change in said dimensions.

13. A method as claimed in claim 10 comprising displaying a waveform, in said graphical representation, representing a variation of said quantity relative to time.

14. A method as claimed in claim 10 comprising generating said graphical representation from a plurality of measured quantities selected from the group consisting of measured curves and measured values.

15. A method as claimed in claim 10 wherein the step of mapping a parameter comprises mapping a plurality of parameters in a single graphical representation, and wherein the step of modifying a control parameter comprises modifying respective control parameters mapped to all of said plurality of parameters dependent on the altered shape of said graphical representation.

16. A method as claimed in claim 10 wherein the step of displaying a graphical representation comprises displaying a curve representing at least one cycle of an electrocardiogram.

17. A method as claimed in claim 10 wherein the step of displaying a graphical representation comprises displaying a curve representing at least one cycle of an intracardial electrogram signal.

18. A method as claimed in claim 10 comprising displaying a measured signal of said quantity for comparison with said graphical representation.

19. A method as claimed in claim 18 comprising comparing said graphical representation with said measured signal by superimposing said graphical representation on the displayed measured signal.

20. A method as claimed in claim 19 wherein the step of superimposing includes automatically adjusting said graphical representation to a scale of said measured signal.

21. A method as claimed in claim 18 comprising displaying said measured signal as varying continuously over time.

22. A method as claimed in claim 21 comprising displaying offset and contrasting portions of said measured signal representing values of said measured signal measured in different time periods.

23. A computer readable medium encoded with a computer program and being loadable into a digital processor for monitoring and controlling operation of an implantable medical device, for causing said digital processor to execute the steps of:
   displaying a graphical representation of a quantity influenced by operation of a medical device;
   mapping parameters relating to control of said medical device onto shapes and relationship of selected portions of said graphical representation;
   allowing manual altering of a shape or relationship of at least one of said portions of said graphical representation, by directly selecting and moving at least one point in said graphical representation, to display a desired operational effect of said medical device on said quantity;
   modifying a control parameter mapped to said graphical representation dependent on said altered shape or relationship, to obtain a modified parameter; and
   communicating said modified parameter to said medical device.

* * * * *